(12) United States Patent
Prakash et al.

(10) Patent No.: US 9,597,510 B2
(45) Date of Patent: Mar. 21, 2017

(54) METHOD AND APPARATUS FOR DETERMINING LEFT VENTRICULAR LUSITROPY

(75) Inventors: Rajan Prakash, Chennai (IN); Rodolphe Katra, Blaine, MN (US)

(73) Assignee: Medtronic, Inc., Minneapolis, MN (US)

( * ) Notice: Subject to any disclaimer, the term of this patent is extended or adjusted under 35 U.S.C. 154(b) by 767 days.

(21) Appl. No.: 13/307,827

(22) Filed: Nov. 30, 2011

(65) Prior Publication Data

US 2012/0143072 A1 Jun. 7, 2012

Related U.S. Application Data

(60) Provisional application No. 61/418,100, filed on Nov. 30, 2010, provisional application No. 61/418,116, filed on Nov. 30, 2010.

(51) Int. Cl.

| | | |
|---|---|---|
| A61B 5/04 | (2006.01) | |
| A61N 1/365 | (2006.01) | |
| A61B 5/11 | (2006.01) | |
| A61B 5/00 | (2006.01) | |
| A61M 5/142 | (2006.01) | |
| A61M 5/172 | (2006.01) | |
| A61N 1/05 | (2006.01) | |
| A61B 5/02 | (2006.01) | |

(52) U.S. Cl.
CPC ...... *A61N 1/36514* (2013.01); *A61B 5/02028* (2013.01); *A61B 5/11* (2013.01); *A61B 5/686* (2013.01); *A61B 5/6869* (2013.01); *A61M 5/14276* (2013.01); *A61M 5/1723* (2013.01); *A61N 1/0587* (2013.01); *A61N 1/36578* (2013.01); *A61M 2005/1726* (2013.01); *A61M 2205/04* (2013.01); *A61M 2205/3303* (2013.01); *A61M 2230/04* (2013.01); *A61N 2001/0585* (2013.01)

(58) Field of Classification Search
USPC .................................. 600/508–509; 607/11
See application file for complete search history.

(56) References Cited

U.S. PATENT DOCUMENTS

| | | |
|---|---|---|
| 3,779,237 A | 12/1973 | Goeltz et al. |
| 5,213,098 A | 5/1993 | Bennett et al. |
| 6,044,297 A | 3/2000 | Sheldon et al. |
| 6,070,101 A | 5/2000 | Struble et al. |
| 6,221,024 B1 | 4/2001 | Miesel |
| 6,738,667 B2 | 5/2004 | Deno et al. |
| 6,871,088 B2 | 3/2005 | Chinchoy |
| 7,662,086 B2 | 2/2010 | Björling |
| 7,682,316 B2 | 3/2010 | Anderson et al. |
| 7,697,972 B2 | 4/2010 | Verard et al. |

(Continued)

OTHER PUBLICATIONS

Lathti, "Signal Processing and Linear Systems," Berkeley-Cambridge Press, Carmichael, CA, 1998. Face page, copy right page, preface and table of contents, 5 pgs.

*Primary Examiner* — Nicole F Johnson
*Assistant Examiner* — Nicole F. Lavert
(74) *Attorney, Agent, or Firm* — Carol F. Barry (57) ABSTRACT

A chronically implanted medical device, connected to a medical electrical lead that includes a sensor, is used to detect diastolic dysfunction. A LV accelerometer signal is sensed through the sensor. Based on the LV accelerometer signal, a determination is made as to whether diastolic dysfunction data exists.

22 Claims, 6 Drawing Sheets

(56) References Cited

U.S. PATENT DOCUMENTS

| | | |
|---|---|---|
| 2004/0097805 A1 | 5/2004 | Verard et al. |
| 2007/0100249 A1 | 5/2007 | Torpo et al. |
| 2007/0179542 A1 | 8/2007 | Prakash et al. |
| 2008/0234771 A1* | 9/2008 | Chinchoy et al. .............. 607/11 |
| 2009/0030292 A1 | 1/2009 | Bartnik et al. |
| 2010/0228136 A1 | 9/2010 | Keel et al. |
| 2011/0015702 A1 | 1/2011 | Ternes et al. |
| 2011/0245628 A1 | 10/2011 | Baker, Jr. et al. |

\* cited by examiner

METHOD AND APPARATUS FOR DETERMINING LEFT VENTRICULAR LUSITROPY

CROSS-REFERENCE TO RELATED APPLICATIONS

This application claims the benefit of U.S. Provisional Application No. 61/418,100, filed on Nov. 30, 2010 entitled "METHOD AND APPARATUS FOR DETERMINING LEFT VENTRICULAR LUSITROPY" and U.S. Provisional Application No. 61/418,116, filed on Nov. 30, 2010 entitled "DETECTION OF RELAXATION ABNORMALITY IN HEART TISSUE". The disclosure of the above applications are incorporated herein by reference in its entirety.

TECHNICAL FIELD

The present disclosure relates generally to implantable medical devices, and, more particularly, to an implantable medical device and associated method for detecting and/or delivering therapy for left ventricular lusitropy.

BACKGROUND

Heart failure is a leading cause of hospitalization in patients older than 65 years old and continues to be associated with high mortality rates. For example, 30 to 40 percent of patients with advanced disease and 5 to 10 percent of patients with mild symptoms die within five to 10 years. Presently, approximately 5 million people in the United States experience heart failure (HF) along with 500,000 newly diagnosed cases per year.

Effective HF therapy can depend upon early detection of lusitropy or diastolic dysfunction). Lusitropy is typically determined through imaging techniques such as echocardiography. Echocardiography is prone to interpretation error depending on the experience of the sonographer. Although nuclear imaging techniques have addressed some of the limitations with echocardiography, echocardiography remains the basic technique to measure diastolic dysfunction.

Another method for determining diastolic dysfunction is presented in U.S. Patent Application Publication 2007/0100249 (now U.S. Pat. No. 7,959,576) to Torpo et al., published May 3, 2007, and entitled Apparatus for Detecting Diastolic Heart Failure. Torpo et al, detetunnes the presence of diastolic heart failure by extracting time duration data during diastole from a sensed IEGM signal. In particular, Torpo relates to using isovolumic relaxation time (IVRT) to detect diastolic heart failure. IVRT occurs during a "still" period or when the heart relaxes without changing volume. In particular, IVRT occurs during the time from the closing of the aortic valve to the opening of the mitralis valve. IVRT is determined from impedance measurements between the left and right ventricles, or between the left ventricle and right atrium. One disadvantage to the method used in Torpo involves determining diastolic heart failure during a pseudonormal state. Torpo et al, may fail to detect a pseudonormal state since the IVRT of a pseudonormal state is about the same as a IVRT for a normal state, as shown, for example in FIG. 1 of Torpo et al. Additionally, Torpo fails to use the LV accelerator signal which provides accurate data as to relaxation abnormalities. It is therefore desirable to determine the presence of relaxation abnormalities in a patient without the limitations associated with the conventional methods used.

DETAILED DESCRIPTION

In the following description, references are made to illustrative embodiments for carrying out the invention. It is understood that other embodiments may be utilized without departing from the scope of the present disclosure.

Figure 1A:
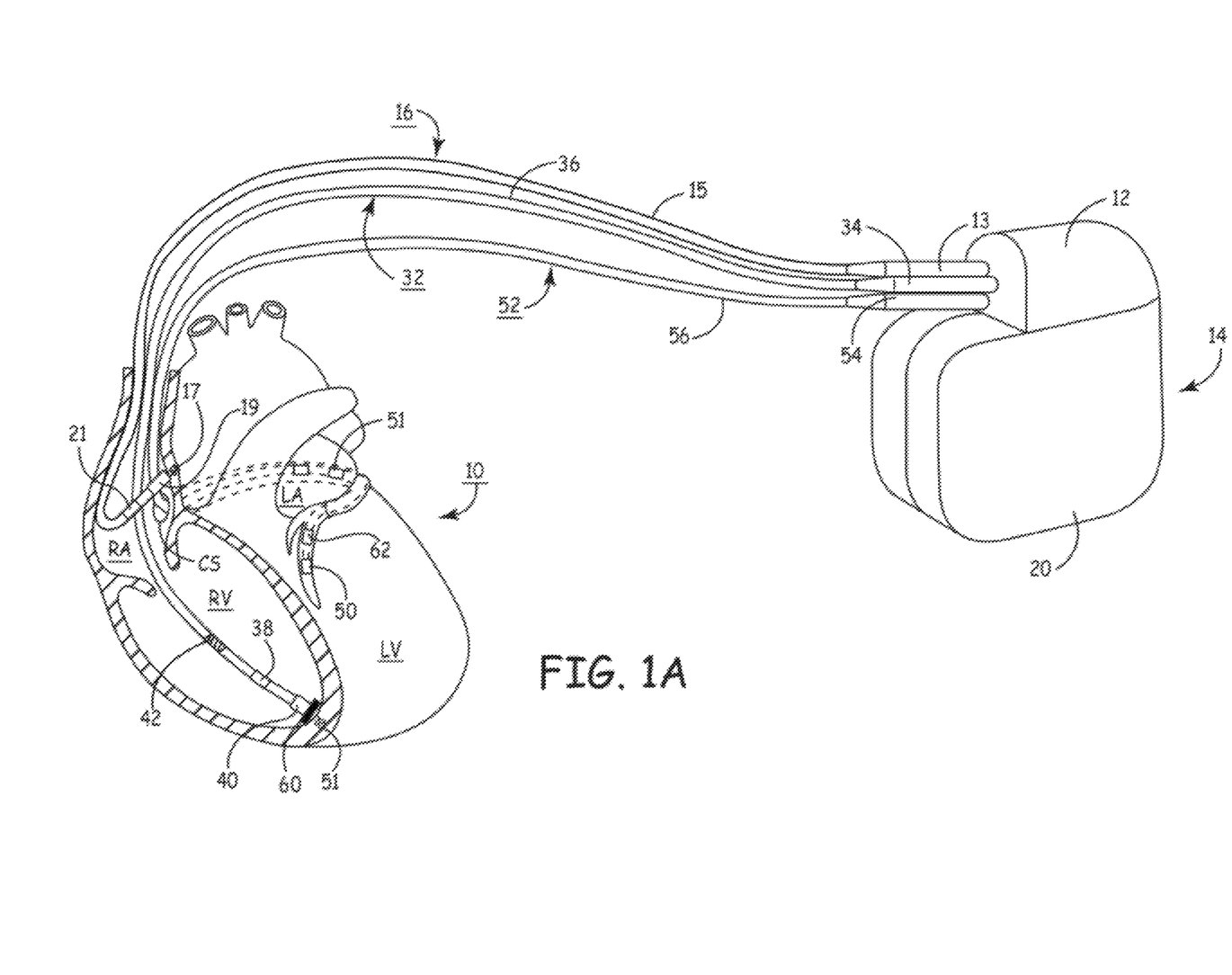
FIG. 1A depicts an implantable, multi-chamber cardiac pacemaker in which one embodiment of the present disclosure may be implemented.
Figure 1B:
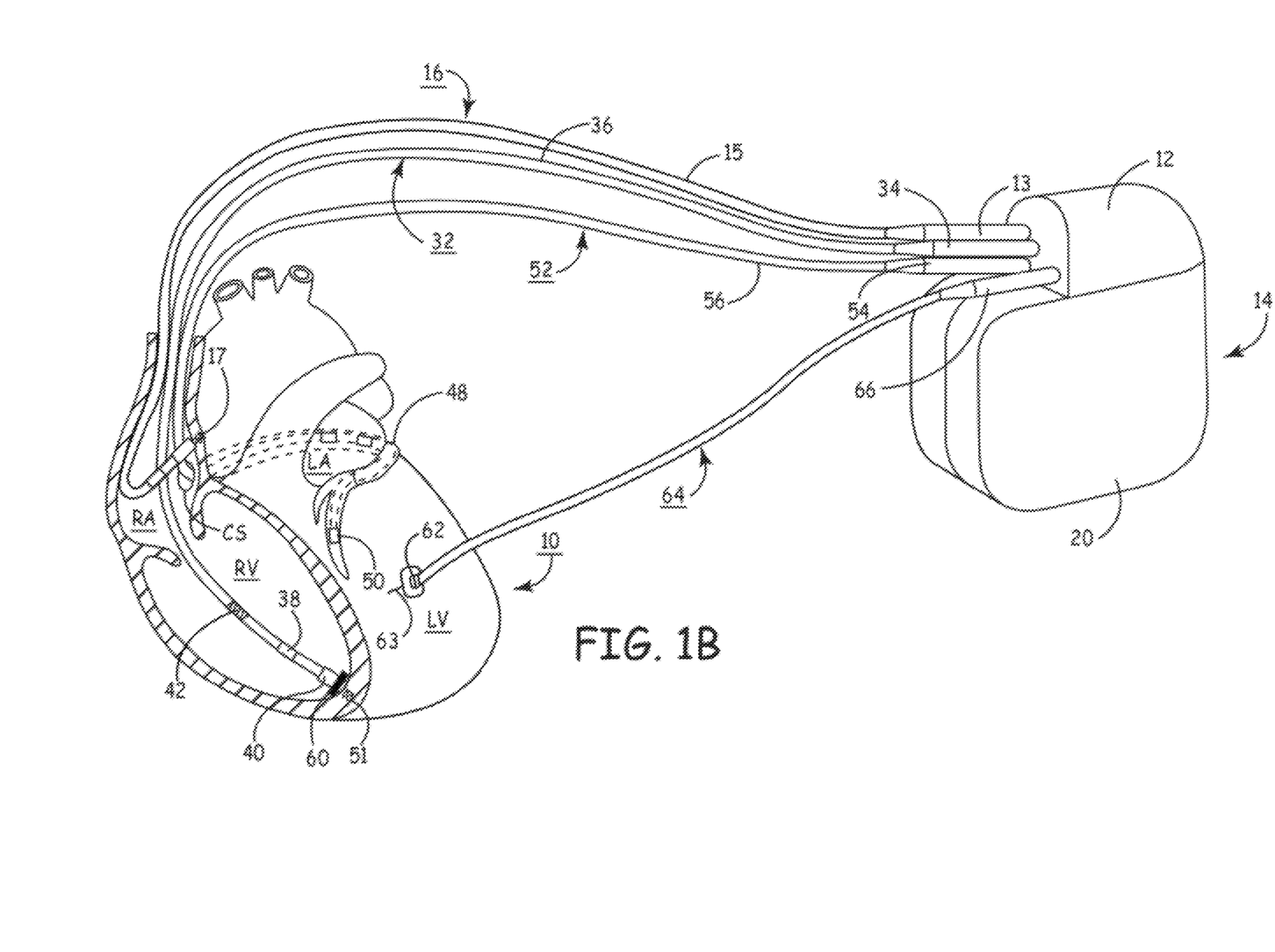
FIG. 1B depicts an implantable, multi-chamber cardiac pacemaker coupled to a patient's heart via transvenous endocardial leads and an additional left ventricular epicardial lead equipped with acceleration sensor.
Figure 2:
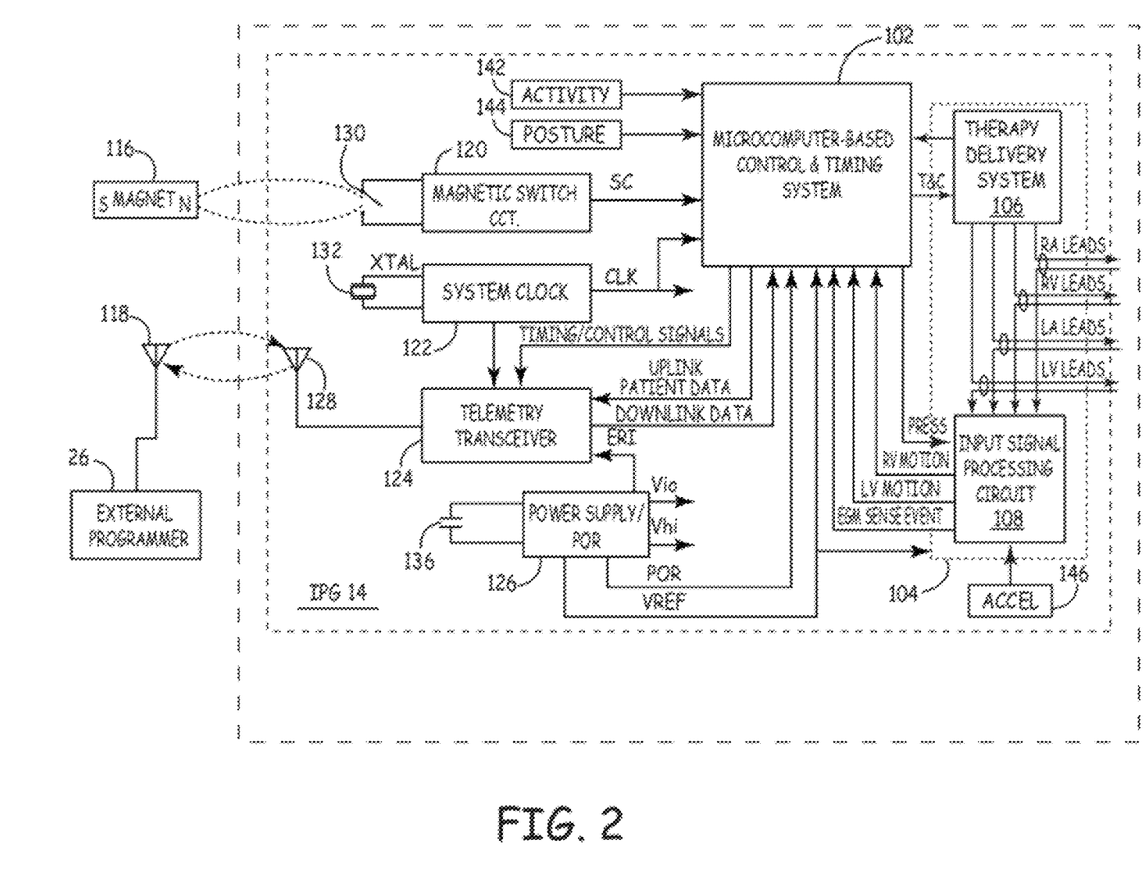
FIG. 2 is a schematic block diagram illustrating one embodiment of a multi-chamber IPG.
Figure 3:
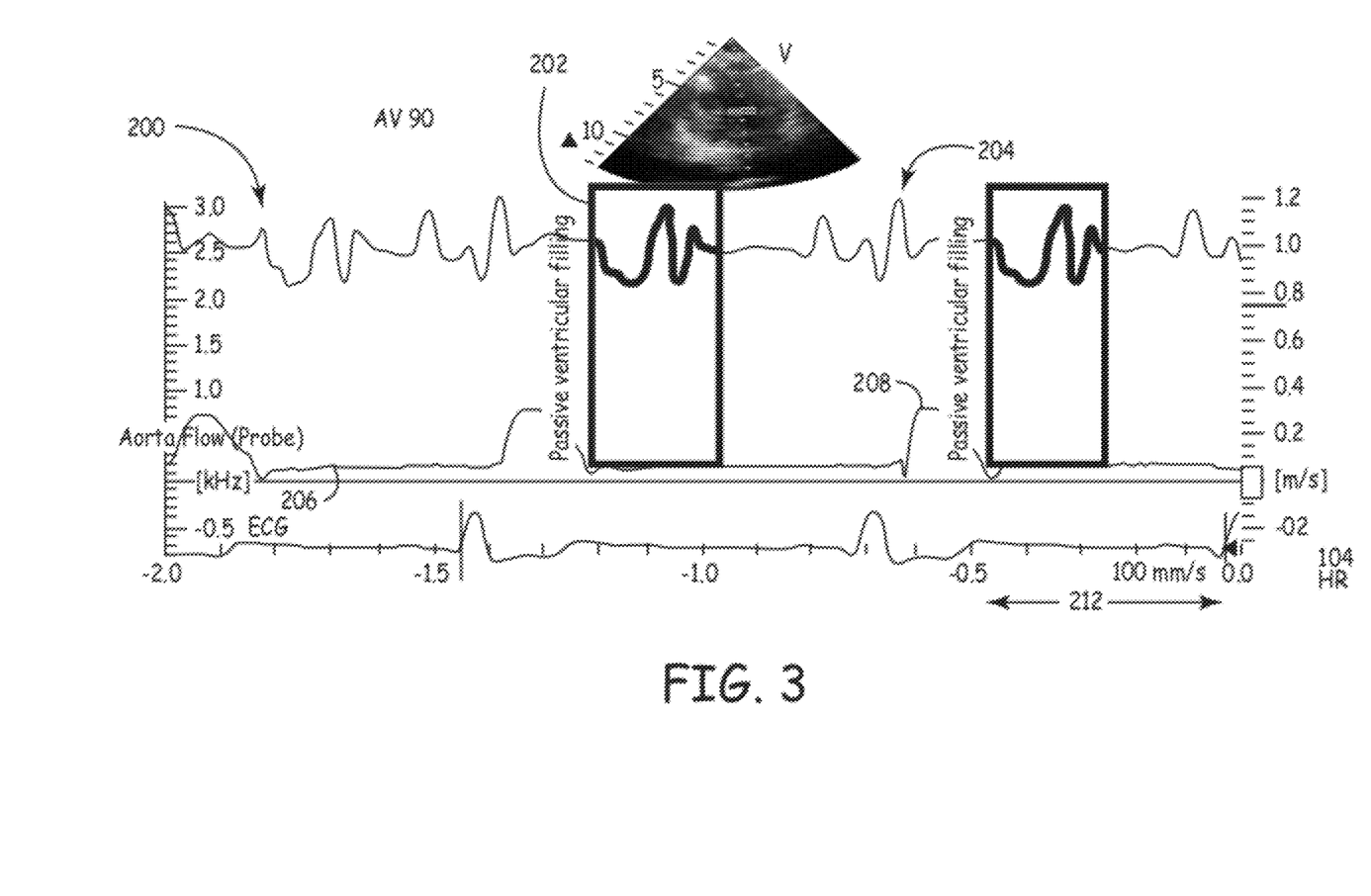
FIG. 3 is an exemplary LV acceleration signal illustrating diastolic metrics.

The present disclosure is directed to monitoring diastolic function using an implantable mechanical sensor affixed to a medical electrical lead connected to an implantable medical device, or located subcutaneously. As disclosed, the implantable medical device that includes a mechanical sensor is able to chronically monitor and manage therapy for diastolic heart failure patients. In particular, the implantable medical device is useful for controlling and/or timing delivery of therapies for diastolic heart failure. FIGS. 1-2 generally depict hardware used to monitor data from a patient in order to determine whether a patient is exhibiting diastolic dysfunction while FIG. 3 is a flow diagram depicting operations used to detect diastolic dysfunction.

FIG. 1A depicts an implantable medical device such as an implantable, multi-chamber cardiac pacemaker 14 in which one embodiment of the present disclosure may be implemented. The multi-chamber pacemaker 14 is provided for sensing intrinsic heart activity and delivering cardiac stimulation pulses as appropriate to one or more heart chambers. Pacemaker 14 may be programmed to operate in any of a number of therapeutic stimulation modes. For example, pacemaker 14 may be configured for delivering cardiac resynchronization stimulation pulses, which control the heart activation sequence for restoring mechanical synchrony within or between one or more heart chambers. Reference is made, for example, to U.S. Pat. No. 6,070,101 (Struble, et al.) and U.S. Pat. No. 6,871,088 (Chinchoy), both of which patents are incorporated herein by reference in their entirety. In other embodiments, pacemaker 14 may deliver extra systolic stimulation pulses as needed to achieve post-extra systolic potentiation effects and thereby provide hemodynamic benefit to the patient. Reference is made to U.S. Pat. No. 5,213,098 (Bennett et al.), and U.S. Pat. No. 6,738,667 (Deno et al.), both of which patents are hereby incorporated herein by reference in their entirety. In various embodiments, pacemaker 14 may be configured to deliver any cardiac stimulation therapy that can be enhanced by or otherwise depends on an optimized AV delay or any other pacing timing control parameters to provide a beneficial effect. Although pacemaker 14 is shown as a multi-chamber pacemaker (sensing and stimulating in three or four heart chambers), it is understood that pacemaker 14 may be modified to operate as a dual chamber pacemaker.

Pacemaker 14 is shown in communication with a patient's heart 10 by way of three leads 16, 32 and 52. The heart 10 is shown in a partially cut-away view illustrating the upper heart chambers, the right atrium (RA) and left atrium (LA), and the lower heart chambers, the right ventricle (RV) and left ventricle (LV), and the coronary sinus (CS) in the right atrium leading into the great cardiac vein 48, which branches to form inferior cardiac veins.

The pacemaker 14, also referred to herein as an "implantable pulse generator" or "IPG," can be implanted subcutaneously in a patient's body between the skin and the ribs. Three transvenous endocardial leads 16, 32 and 52 connect the IPG 14 with the RA, the RV and the LV, respectively. Each lead has at least one electrical conductor and pace/sense electrode. A remote indifferent can electrode 20 is formed as part of the outer surface of the housing of the IPG 14. The pace/sense electrodes and the remote indifferent can electrode 20 can be selectively employed to provide a number of unipolar and bipolar pace/sense electrode combinations for pacing and sensing functions.

The depicted bipolar endocardial RA lead 16 is passed through a vein into the RA chamber of the heart 10, and the distal end of the RA lead 16 may be attached to the RA wall using a fixation member 17. The bipolar endocardial RA lead 16 is formed with a connector 13 fitting into a connector bore of IPG connector block 12 that is coupled to a pair of electrically insulated conductors within lead body 15 and connected with distal tip RA pace/sense electrode 19 and proximal ring RA pace/sense electrode 21 provided for achieving RA stimulation and sensing of RA electrogram (EGM) signals.

Bipolar, endocardial RV lead 32 is passed through the RA into the RV where its distal end, carrying tip RV pace/sense electrode 40 and ring RV pace/sense electrode 38, is fixed in place in the RV apex by a distal fixation member 41. The RV lead 32 is formed with a connector 34 fitting into a corresponding connector bore of IPG connector block 12 that is coupled to a pair of electrically insulated conductors within lead body 36 and connected with distal tip RV pace/sense electrode 40 and proximal ring RV pace/sense electrode 38 provided for RV stimulation and sensing of RV EGM signals. RV lead 32 may optionally include a sensor 60 responsive to RV wall acceleration, such as a heart sound sensor. One or more exemplary heart sound sensors may be seen with respect to U.S. Pat. No. 7,682,316 issued Mar. 23, 2010, entitled IMPLANTABLE HEART SOUND SENSOR WITH NOISE CANCELLATION, and assigned to the assignee of the present invention, the disclosure of which is incorporated by reference in its entirety herein.

RV acceleration sensor 60 may be positioned into or proximate the RV apex for detecting acceleration of the RV apical region. In other embodiments, RV acceleration sensor 60 may be disposed at other locations along the RV for sensing RV acceleration.

RV lead 32 may further include a blood pressure sensor 42. Blood pressure sensor 42 may be used for monitoring cardiac function and, in some embodiments, used in combination with either of the right or left wall acceleration signals for optimizing pacing timing control parameters. A RV blood pressure sensor and its use in monitoring cardiac function are generally described in U.S. Pat. No. 6,221,024 (Miesel, Apr. 24 2001), hereby incorporated herein by reference in its entirety. It is understood that any combination of electrodes and physiological sensors, including, for example, pressure sensors, blood chemistry sensors, flow sensors, acoustical sensors, and impedance sensors, may be included in IPG 14 or an associated lead system. Such sensors may be used in conjunction with an accelerometer for sensing cardiac signals and optimizing cardiac pacing timing control parameters as will be described in greater detail below.

Coronary sinus lead 52 is passed through the RA, into the CS and further into a cardiac vein 48 to extend the distal LV CS pace/sense electrode 50 alongside the LV chamber to achieve LV stimulation and sensing of LV EGM signals. The LV CS lead 52 is coupled at the proximal end connector 54 into a bore of IPG connector block 12. A small diameter lead body 56 is typically selected in order to lodge the distal LV CS pace/sense electrode 50 deeply in a cardiac vein branching from the great cardiac vein 48.

In one embodiment of the present disclosure, one of three leads 16, 32 and 52 includes sensor 62. For example, as depicted, CS lead 52 is provided with a sensor 62 capable of generating a signal proportional to the acceleration of the left ventricular free wall. Sensor 62 may be embodied as a uniaxial, biaxial, or triaxial (or multiaxial) accelerometer contained in a capsule of a relatively small size and diameter such that it may be included in a coronary sinus lead without substantially increasing the lead diameter or impairing the ability to steer the lead to a left ventricular stimulation and sensing site. For the purposes of assessing cardiac function using an accelerometer deployed in operative relation to the left ventricle, a uniaxial accelerometer configured to generate a signal responsive to LV motion substantially along one axis, e.g. longitudinal acceleration, may be sufficient. Radial acceleration might be procured with multiaxial accelerometers to provide more detailed information about LV motion. Sensor 62 may alternatively be provided as another type of transducer such as a transducer having an optical, acoustical, piezoelectric, inductive, capacitive, resistive, or other elements which produce a variable signal proportional to ventricular acceleration or from which variations in ventricular acceleration can be derived.

Sensor 62 is located on CS lead 52 such that when CS lead 52 is positioned for LV stimulation and sensing, sensor 62 is located over the left ventricle and is typically positioned approximately over the left ventricular free wall mid-lateral to mid-basal segments. The depicted positions of the leads and electrodes shown in FIG. 1A in or about the right and left heart chambers are approximate and merely illustrate one of many possible configurations. For example, a left ventricular acceleration sensor 62 may alternatively be located on CS lead 52 such that sensor 62 is positioned along the great cardiac vein, or along any accessible inferior cardiac vein. Furthermore, it is recognized that alternative leads and pace/sense electrodes that are adapted for placement at stimulation or sensing sites on or in or relative to the RA, LA, RV and LV may be used in conjunction with the present disclosure.

The sensing apparatus 87 may further include one or more pressure sensors, posture sensors (e.g., 2-D or 3-D accelerometers), heart sound sensors, activity sensors, perfusion sensors etc. and/or the normalized ejection time % (ET/RR %) to monitor, or be able to determined through monitored data, one or more heart-related physiological parameters such as, e.g., patient posture, ejection time, stroke volume, cardiac output, pre-ejection time, filling time, E/A ratio, E/E', and E deceleration time etc.

In some embodiments, LV CS lead 52 could bear a proximal LA CS pace/sense electrode 51 positioned along CS lead body 56 such that it is disposed proximate the LA for use in stimulating the LA and/or sensing LA EGM signals. In that case, the lead body 56 would encase an insulated lead conductor extending proximally from the more proximal LA CS pace/sense electrode(s) and terminating at lead connector 54.

FIG. 1B depicts an implantable, multi-chamber cardiac pacemaker coupled to a patient's heart via transvenous endocardial leads and an additional left ventricular epicardial lead equipped with acceleration sensor 62. Patients may have previously had a transvenous lead system implanted that includes a coronary sinus lead 52 that is not equipped with an acceleration sensor. Such patients may benefit from the placement of an epicardial lead 64 equipped with an acceleration sensor 62 coupled to IPG 14 via a connector 66 so as to provide an LV acceleration signal.

Epicardial lead 64 is provided with a fixation member 63 which may serve additionally as a pacing and/or sensing electrode. In some cases, an epicardial lead may be preferred over a coronary sinus lead due to the difficulty in advancing a coronary sinus lead into a relatively small cardiac vein over the LV free wall. Placement of a coronary sinus lead can be a cumbersome task due to the tortuosity of the cardiac veins. Therefore, it may be desirable, at least in some patients, to provide an epicardial lead that can be positioned on the LV lateral wall for stimulation, EGM sensing and acceleration sensing, thereby eliminating the need for a coronary sinus lead. Alternatively, it may be desirable to deploy a small diameter coronary sinus lead for LV stimulation and EGM sensing with a separate LV epicardial lead positioned for sensing LV acceleration.

The embodiment generally shown in FIG. 1B may be used for specific selection of cardiac stimulation/sensing sites. With epicardial lead 64 fixed at a desired location for assessing LV acceleration, the effect of pacing at different locations in one or more heart chambers can be evaluated by deploying the transvenous pacing leads 16, 32 and 52 to different locations. In particular, coronary sinus lead 52 may be advanced to different locations until an optimal location is identified based on analysis of the signal from LV acceleration sensor 62. By providing acceleration sensor 62 on a separate, epicardial lead 64, the position of LV pace/sense electrode 50, provided on coronary sinus lead 52, may be adjusted independently of sensor 62. In one or more embodiments, if the position of pace/sense electrode 50 needs adjusting, acceleration sensor 62 may remain fixed at a desired measurement site on the LV epicardial wall thereby allowing comparisons to be made between measurements repeated at the same location for different pacing intervals and/or pacing sites.

Any type of transducer may be provided for sensing or deriving ventricular wall acceleration corresponding to the right and/or left ventricle provided such transducers are hermetically sealed, fabricated (at least on the exterior surfaces) of substantially biocompatible materials and appropriately dimensioned for a given application. In addition to transducers that sense acceleration, transducers which sense velocity, displacement or force may be used from which an acceleration component can be derived. With respect to appropriate dimension, a transducer intended for transvenous deployment should be adapted for catheter or over-the-wire delivery. Thus, the radial dimension should generally be on the order of less than about 11 French. The transducer should be somewhat supple with a longitudinal dimension that allows the transducer to safely navigate the venous system, pass through the coronary sinus and enter vessels branching from the coronary sinus. These dimensions are less limited for a transducer intended for deployment through a portion of the chest (e.g., a thoracotomy) with a fixation mechanism adapted to mechanically coupled adjacent the epicardium or pericardium. The dimensions may be relaxed to a greater extent if the epicardium receives the transducer, and to a lesser extent, to a portion of the pericardium. One example of appropriate fixation apparatus for epicardial application is a lead having a distal fixation helix that is screwed into the surface of the epicardium. For pericardial fixation a sealing member (e.g., compressible gasket or opposing members on each side of the pericardial sac) may be used in addition to an active fixation member such as a helical member.

As is also known in the art related to sensors and transducers, accelerometers can be described as two transducers, a primary transducer (typically a single-degree-of-freedom vibrating mass which converts the acceleration into a displacement), and a secondary transducer that converts the displacement (of a seismic mass) into an electrical signal. Most accelerometers use a piezoelectric element as a secondary transducer. Piezoelectric devices, when subjected to a strain, output a voltage proportional to the strain, although piezoelectric elements cannot provide a signal under static (e.g., constant acceleration) conditions. Accelerometers characteristics include range of acceleration, frequency response, transverse sensitivity (i.e. sensitivity to motion in the non-active direction), mounting errors, temperature and acoustic noise sensitivity, and mass.

One type of primary transducer, which describes the internal mechanism of the accelerometer, includes a spring-retained seismic mass. In most accelerometers, exerted acceleration forces a damped seismic mass that is restrained by a spring, so that it moves relative to the transducer casing along a single axis. The secondary transducer then responds to the displacement and/or force associated with the seismic mass. The displacement of the mass and the extension of the spring are proportional to the acceleration only when the oscillation is below the natural frequency. Another accelerometer type uses a double-cantilever beam as a primary transducer which can be modeled as a spring-mass-dashpot.

Types of secondary transducers, which describe how the electric signal is generated from mechanical displacement, include: piezoelectric, potentiometric, reluctive, servo, strain gauge, capacitive, vibrating element, etc. These are briefly described as an introduction for the uninitiated.

Piezoelectric transducers are often used in vibration-sensing accelerometers, and sometimes in shock-sensing devices. The piezoelectric crystals (e.g., often quartz or ceramic) produce an electric charge when a force is exerted by the seismic mass under some acceleration. The quartz plates (two or more) are preloaded so that a positive or negative change in the applied force on the crystals results in a change in the electric charge. Although the sensitivity of piezoelectric accelerometers is relatively low compared with other types of accelerometers, they have the highest range (up to 100,000 g's) and frequency response (over 20 kHz).

Potentiometric accelerometers utilize the displacement of the spring-mass system linked mechanically to a wiper arm, which moves along a potentiometer. The system can use gas, viscous, magnetic-fluid, or magnetic damping to minimize acoustic noise caused by contact resistance of the wiper arm. Potentiometric accelerometers typically have a frequency range from zero to 20-60 Hz, depending on the stiffness of the spring, and have a high-level output signal. They also have a lower frequency response than most other accelerometers, usually between 15-30 Hz.

Reluctive accelerometers use an inductance bridge, similar to that of a linear variable differential transducer to produce an output voltage proportional to the movement of the seismic mass. The displacement of the seismic mass in inductance-bridge accelerometers causes the inductances of two coils to vary in opposing directions. The coils act as two arms of an inductance bridge, with resistors as the other two arms. The AC output voltage of the bridge varies with applied acceleration. A demodulator can be used to convert the AC signal to DC. An oscillator can be used to generate the required AC current when a DC power supply is used, as long as the frequency of the AC signal is far greater than that of the frequency of the acceleration.

In servo accelerometers, acceleration causes a seismic mass "pendulum" to move. When motion is detected by a position-sensing device, a signal is produced that acts as the error signal in the closed-loop servo system. After the signal has been demodulated and amplified to remove the steady-state component, the signal is passed through a passive damping network and is applied to a torquing coil located at the axis of rotation of the mass. The torque developed by the torquing coil is proportional to the current applied, and counteracts the torque acting on the seismic mass due to the acceleration, preventing further motion of the mass. Therefore, the current through the torquing coil is proportional to acceleration. This device can also be used to measure angular acceleration as long as the seismic mass is balanced. Servo accelerometers provide high accuracy and a high-level output at a relatively high cost, and can be used for very low measuring ranges (well below 1 g).

Strain gauge accelerometers, often called "piezoresistive" accelerometers, use strain gauges acting as arms of a Wheatstone bridge to convert mechanical strain to a DC output voltage. The gauges are either mounted to the spring, or between the seismic mass and the stationary frame. The strain gauge windings contribute to the spring action and are stressed (i.e., two in tension, two in compression), and a DC output voltage is generated by the four arms of the bridge that is proportional to the applied acceleration.

These accelerometers can be made more sensitive with the use of semiconductor gauges and stiffer springs, yielding higher frequency response and output signal amplitude. Unlike other types of accelerometers, strain gauge accelerometers respond to steady-state accelerations.

In a capacitive accelerometer a change in acceleration causes a change in the space between the moving and fixed electrodes of a capacitive accelerometer. The moving electrode is typically a diaphragm-supported seismic mass or a flexure-supported, disk-shaped seismic mass. The element can act as the capacitor in the LC or RC portion of an oscillator circuit. The resulting output frequency is proportional to the applied acceleration.

In a vibrating element accelerometer, a very small displacement of the seismic mass varies the tension of a tungsten wire in a permanent magnetic field. A current through the wire in the presence of the magnetic field causes the wire to vibrate at its resonant frequency (like a guitar string). The circuitry then outputs a frequency modulation (deviation from a center frequency) that is proportional to the applied acceleration. Although the precision of such a device is high, it is quite sensitive to temperature variations and is relatively expensive.

FIG. 2 is a schematic block diagram illustrating one embodiment of a multi-chamber IPG 14. IPG 14 is configured to provide a cardiac stimulation therapy and for processing a left ventricular acceleration signal input from any of the types of transducers described above or any other type of transducer sensitive to ventricular acceleration for use in optimizing pacing timing control parameters to achieve an optimized cardiac function metric.

As shown, IPG 14 includes a microprocessor-based control and timing system 102 for controlling the functions of IPG 14 by executing firmware and programmed software (or computer instructions) algorithms stored in associated memory such as RAM and ROM. Preferably, computer instructions for performing the method of detecting and/or delivering therapy for diastolic dysfunction are stored in RAM. Control and timing system 102 may also include a watchdog circuit, a DMA controller, a block mover/reader, a CRC calculator, and other specific logic circuitry coupled together by on-chip data bus, address bus, power, clock, and control signal lines in paths or trees in a manner known in the art. It will also be understood that control and timing functions of IPG 14 can be accomplished with dedicated circuit hardware or state machine logic rather than a programmed microcomputer.

The IPG 14 includes interface circuitry 104 for receiving signals from sensors and pace/sense electrodes located at specific sites of the patient's heart chambers and delivering cardiac stimulation aimed at achieving a therapeutic benefit. The interface circuitry 104 therefore includes a therapy delivery system 106 intended for delivering cardiac stimulation pulses under the control of control and timing system 102. Delivery of stimulation pulses in one or more heart chambers is controlled in part by the selection of programmable timing intervals, which can include atrial-atrial (A-A), atrial-ventricular (A-V), and ventricular-ventricular (V-V) intervals and may further include extra systolic intervals or other timing intervals to one or more chambers according to the type of therapy being delivered and the programmed operating mode.

Physiologic input signal processing circuit 108 is provided for receiving cardiac electrogram (EGM) signals for determining a patient's heart rhythm. Physiologic input signal processing circuit 108 additionally receives signals from left ventricular acceleration sensor 62, and RV acceleration sensor 60 and RV pressure sensor 42 when used, processes these signals and provides signal data to control and timing system 102 for further signal analysis. For purposes of illustration, a set of lead connections are depicted for making electrical connections between the therapy delivery system 106 and the input signal processing circuit 108 and sets of pace/sense electrodes, acceleration sensors, and any other physiological sensors located in operative relation to the RA, LA, RV and LV.

Control and timing system 102 controls the delivery of cardiac stimulation pulses at selected timing intervals intended to improve heart function or otherwise alleviate a heart condition as needed. Selection of the programmable intervals includes an analysis of a wall acceleration signal obtained from LV acceleration sensor 62 as will be described in greater detail below. In particular, a ventricular wall acceleration signal is analyzed according to user-selected optimization criteria to optimize pacing timing control parameters, such as AV, AA and VV delays. An AV delay may be controlled by controlling a timed escaped interval following a right atrial or left atrial pacing pulse or sensed depolarization and a subsequent ventricular pacing pulse delivered in either the right or left ventricle. An AA delay may be used to control the relative timing between depolarizations of the right and left atria. Likewise, a VV delay may be used to control the relative timing between depolarizations of the right and left ventricles.

The methods described herein for optimizing a pacing timing parameter using a LV accelerometer signal may be applied to any timing parameter used to control the delivery of any pacing therapy. Accordingly, leads in communication with the patient's heart could additionally include high-voltage cardioversion or defibrillation shock electrodes.

A battery 136 provides a source of electrical energy to power components and circuitry of IPG 14 and provide energy for delivering electrical impulses to the heart. The typical energy source is a high energy density, low voltage battery 136 coupled with a power supply/POR circuit 126 having power-on-reset (POR) capability. The power supply/POR circuit 126 provides one or more low voltage power (Vlo), the POR signal, one or more reference voltage (VREF) sources, current sources, an elective replacement indicator (ERI) signal, and, in the case of a cardioversion/defibrillator capabilities, high voltage power (Vhi) to the therapy delivery system 106. A power supply and interconnections with IPG 14 components may correspond to configurations known in the art.

Electronic IPG circuitry typically employs clocked CMOS digital logic ICs that require a clock signal CLK provided by a piezoelectric crystal 132 and system clock 122 coupled thereto as well as discrete components, e.g., inductors, capacitors, transformers, high voltage protection diodes, and the like that are mounted with the ICs to one or more substrate or printed circuit board. In FIG. 2, each CLK signal generated by system clock 122 is routed to all applicable clocked logic via a clock tree. The system clock 122 provides one or more fixed frequency CLK signal that is independent of the battery voltage over an operating battery voltage range for system timing and control functions and in formatting uplink telemetry signal transmissions in the telemetry I/O circuit 124.

The RAM registers included in microprocessor-based control and timing system 102 may be used for storing data compiled from sensed EGM signals, acceleration signals, and/or relating to device operating history or other sensed physiologic parameters for uplink telemetry transmission upon receipt of a retrieval or interrogation instruction via a downlink telemetry transmission. Criteria for triggering data storage can be programmed via downlinked instructions and parameter values.

Physiologic data, including ventricular acceleration data and data derived therefrom, may be stored on a triggered or periodic basis or by detection logic within the physiologic input signal processing circuit 108. Physiologic input signal processing circuit 108 can be configured to extract data of a complete relaxation cycle or complete relaxation period from a sensed signal such as LV accelerometer signal. The complete relaxation cycle or period generally occurs after the T wave and before the P wave. The extracted complete relaxation cycle can be compared to baseline data to determine whether diastolic dysfunction exists. In yet another embodiment, physiologic input signal processing circuit 108 can be configured to extract data of a complete contraction cycle or complete contraction period from a sensed signal such as LV accelerometer signal. The complete contraction period is the PQRS complex. The extracted complete contraction cycle can be compared to baseline data to determine whether diastolic dysfunction exists. Optionally, the comparison operation between the complete relaxation data and the baseline data or the complete contraction data and the baseline data can be performed at the physiologic input signal processing circuit 108. Alternatively, a separate electronic or computer instruction module, directly connected to the signal processing circuit 108, can perform comparisons between sensed data and baseline data. Template matching can be performed between the data sensed from the LV accelerometer signal (e.g. complete relaxation data, complete contraction data etc.) and the baseline data. Template matching is a technique well known in signal processing. In one or more other embodiments, waveform comparison between the sensed signal and the baseline signal data can also be performed by signal processing circuit 108.

In still yet another embodiment, the magnitude of diastolic dysfunction can be determined. The ranking can be formed in a number of ways. To illustrate, diastolic dysfunction could be ranked from 1 to 10 where a ranking of 10 indicates the worst case of diastolic dysfunction. If data obtained from the LV accelerometer signal indicates severe diastolic dysfunction, the data may be assigned a value of 10. Optionally, after detection of diastolic dysfunction, a wired or wireless notification signal can be automatically sent to a healthcare provider and/or patient as to the detection of diastolic dysfunction.

In some cases, the IPG 14 includes a magnetic field sensitive switch 130 that closes in response to a magnetic field, and the closure causes a magnetic switch circuit 120 to issue a switch closed (SC) signal to control and timing system 102 which responds in a magnet mode. For example, the patient may be provided with a magnet 116 that can be applied over the subcutaneously implanted IPG 14 to close switch 130 and prompt the control and timing system to deliver a therapy and/or store physiologic data. Event related data, e.g., the date and time and current pacing parameters, may be stored along with the stored physiologic data for uplink telemetry in a later interrogation session.

Uplink and downlink telemetry capabilities are provided to enable communication with either a remotely located external medical device or a more proximal medical device on or in the patient's body. Stored EGM, or ventricular wall acceleration data as well as real-time generated physiologic data and non-physiologic data can be transmitted by uplink RF telemetry from the IPG 14 to the external programmer or other remote medical device 26 in response to a downlink telemetered interrogation command. As such, an antenna 128 is connected to radio frequency (RF) transceiver circuit 124 for the purposes of uplink/downlink telemetry operations. Telemeteric communication of both analog and digital data between antenna 128 and an external device 26, also equipped with an antenna 118, may be accomplished using numerous types of telemetry systems known in the art for use in implantable devices.

In accordance with one embodiment of the present disclosure, a clinician or other user uses external programmer 26 to program a selected optimization metric for use in an automatic determination of an optimal pacing timing control parameter. As will be described in greater detail below, a user interacting with external programmer may provide programming commands to IPG 14 during downlink telemetry indicating a diastolic, systolic or combination of diastolic and systolic optimization metrics to be used by IPG 14 in executing timing parameter optimization algorithms.

The physiologic input signal processing circuit 108 includes at least one electrical signal amplifier circuit for amplifying, processing and in some cases detecting sense events from characteristics of the electrical sense signal or sensor output signal. The physiologic input signal processing circuit 108 may thus include a plurality of cardiac signal sense channels for sensing and processing cardiac signals from sense electrodes located in relation to a heart chamber.

Each such channel typically includes a sense amplifier circuit for detecting specific cardiac events and an EGM amplifier circuit for providing an EGM signal to the control and timing system 102 for sampling, digitizing and storing or transmitting in an uplink transmission. Atrial and ventricular sense amplifiers include signal processing stages for detecting the occurrence of a depolarization associated with a P-wave or R-wave, respectively, and providing an atrial sense or ventricular sense event signal to the control and timing system 102. Timing and control system 102 responds in accordance with its particular operating mode to deliver or modify a stimulation therapy, if appropriate, or to accumulate data for uplink telemetry transmission in a variety of ways known in the art. Cardiac stimulation pulse delivery is generally determined based on EGM signal input according to the particular operating mode in effect. However, the intervals at which stimulation pulses are delivered may be determined, at least in part, based on an assessment of ventricular wall acceleration data as will be described below.

As such, input signal processing circuit 108 further includes signal processing circuitry for receiving, amplifying, filtering, averaging, digitizing or otherwise processing the LV wall acceleration sensor signal. Acceleration signal processing circuitry is further provided for detection and/or determination of one or more acceleration signal characteristics such as maximum and minimum peak amplitudes, slopes, integrals, or other time or frequency domain signal characteristics that may be used as metrics of cardiac function. Acceleration data from an LV wall acceleration sensor signal are made available to control and timing system 102 via LV MOTION signal line. LV acceleration data may be used for monitoring cardiac function and is used in algorithms performed for identifying AV timing intervals which meet user-selected optimization criteria. If an RV acceleration sensor is present, an additional RV MOTION signal line provides RV acceleration signal data to control and timing system 102. A PRESSURE signal line provides blood pressure data received from a blood pressure sensor, which may be placed in any of the chambers of the heart or along the circulation system, to control and timing 102.

IPG 14 may further include sensors incorporated in or on the IPG housing. An activity sensor 142 provides a signal to control and timing system 102 responsive to the level of patient activity. A posture sensor 144 provides a signal to control and timing system 102 responsive to the patient's posture. Activity sensor 142 and posture sensor 144 may be used by control and timing system 102 in controlling IPG functions, for example in controlling the delivery of pacing therapies according to a patient's metabolic need and/or posture. According to some embodiments of the present disclosure, activity sensor 142 and posture sensor 144 may be used in verifying stable conditions required for performing timing parameter optimization using an LV acceleration signal. The use of activity sensors in implantable cardiac stimulation devices for determining a level of patient activity and/or providing rate-responsive pacing is known in the art. A posture sensor for use in an implantable medical device is generally described in U.S. Pat. No. 6,044,297 (Sheldon, et al.), hereby incorporated herein by reference in its entirety.

An auxiliary accelerometer 146 may be provided in or on the IPG housing and coupled to input signal processing circuit 108 for use in correcting an LV (or RV) accelerometer signal for noise. Auxiliary accelerometer 146 may be included in an implanted system and positioned at any non-cardiac location to provide a signal that may be used to adjust the LV acceleration signal to remove or minimize the effects of gravity, postural changes, patient activity, or any other non-cardiac acceleration signal sources.

IMD 14 along with the accelerometers is configured to monitor diastolic phases. During normal cardiac function, the left ventricle fills during two diastolic phases, a passive filling phase and an active filling phase. The passive filling phase occurs first as the ventricle relaxes following ventricular systole. Ventricular relaxation causes pressure within the left ventricle to fall, allowing the mitral valve between the left atrium and left ventricle to open. Blood flows into the left ventricle through the left atrium during the passive filling phase due to a pressure difference across the mitral valve. As the passive filling rate slows, the left atrium contracts, actively contributing to ventricular filling. The force generated by the actively contracting left atrium forces more blood into the ventricle. Atrial contribution to ventricular filling helps to maintain an adequate preload for ventricular contraction. According to the Frank-Starling law, the ventricles contract more forcefully during systole when filled to a greater degree during diastole.

Diastole is a period between contractions of the atria or the ventricles during which blood enters the relaxed chambers from the systemic circulation and the lungs. Ventricular diastole begins with the onset of the second heart sound and ends with the first heart sound. Systole relates to the contraction, or period of contraction, of the heart, especially of the ventricles.

Generally, cardiac stroke volume increases as cardiac filling increases. During many disease states or during various physiologic conditions such as exercise, an overlap between the phases of active atrial contraction and passive left ventricular filling can occur. Overlap between the phases of active atrial contraction and passive left ventricular filling can result in reduced atrial contribution to ventricular filling as the pressure gradient across the mitral valve is reversed from normal upon the onset of systole. This contributes to aphysiologic conditions including mitral regurgitation and flow reversal through the pulmonary vein, manifesting itself with a clinical symptom referred to as "pacemaker syndrome". If atrial contraction occurs too late after the passive filling phase, ventricular contraction may have already begun, closing the mitral valve. Late atrial contraction may cause the atria to contract against a closed or partially closed valve, which can result in retrograde flow. Early atrial contraction, prior to the end of the passive filling phase, results in fusion of the passive and active filling phases. The force available from the contracting atria can be under-utilized when blood is forced into an empty or only partially filled ventricle, which reduces the overall filling of the left ventricle and can result in reduced effectiveness of systolic contraction.

Figure 4:
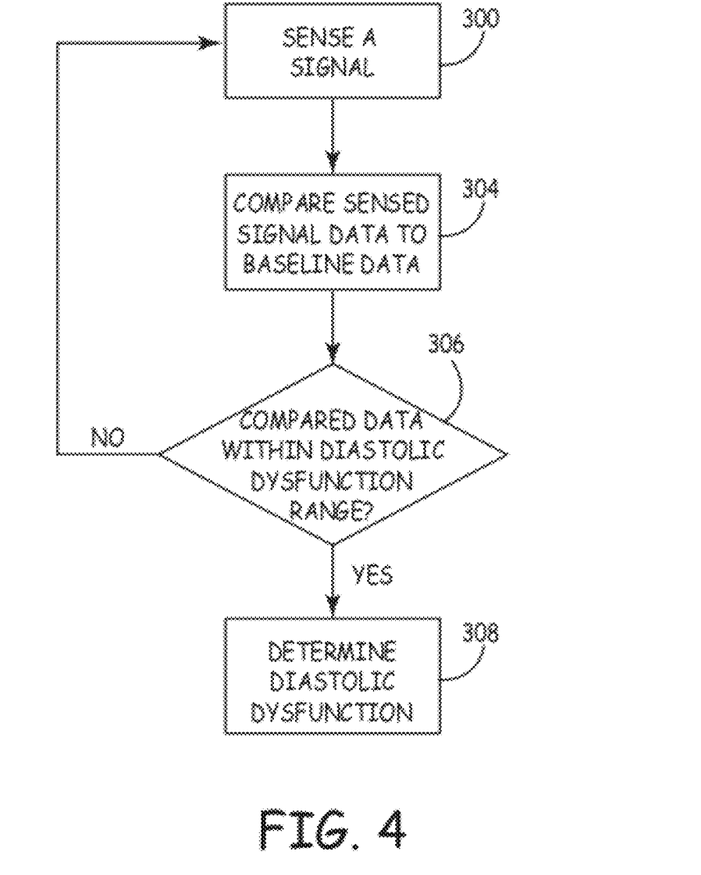
FIG. 4 is a flow diagram summarizing steps performed in a method for determining whether a patient exhibits diastolic dysfunction.

While FIGS. 1-2 and the accompanying text describe pacemaker 14 configured to sense electrical activity of a selected organ via one or more signals that may be monitored (e.g., using electrodes, mechanical sensor) from locations in or around a selected organ (heart, kidneys etc.), FIG. 4 is a flow diagram summarizing steps performed in a method for determining whether a patient exhibits diastolic dysfunction and treatment thereof through the use of a chronically implanted medical device.

At operation 300 of FIG. 4, a signal is sensed through a mechanical sensor (e.g. heart sound sensor etc.) coupled to a lead and/or housing of an implantable medical device 14. The sensed signal is transmitted to the microprocessor 102 to undergo signal processing. Exemplary techniques for decomposing a signal can include techniques as presented in Signal Processing & Linear Systems, B. P. Lahti 1998), which is incorporated by reference herein. Signal processing parses a signal into data. FIG. 3 is an exemplary LV acceleration signal. A brief review of diastolic function as to acceleration signal 200 is presented. LV acceleration signal 200 is shown in time with respect to a simultaneously recorded electrocardiogram (ECG) signal. During optimal physiologic diastolic coupling, both passive and active 206 filling phases occur without truncation of ventricular filling prior to ventricular contraction. Passive LV filling occurs as the LV myocardium relaxes during a passive filling phase indicated by the bracketed signal 202. At the end of LV relaxation, passive filling slows and the LA contracts, providing active filling of the LV, often referred to as the "atrial kick." During ventricular diastole, the LV acceleration signal 200 thus includes a first filling phase signal 202 associated with LV passive filling. The first filling phase signal 202 is often characterized by alternating positive and negative peaks, morphologically resembling that of a "W". In the example shown, the first filling phase signal 202 is distinguishable from a second filling phase signal peak 204, associated with LV active filling due to atrial contraction. Changes in the timing of atrial contraction alter the relative timing and morphology of the passive filling phase signal 202 and the active filling phase peak 204.

The LV acceleration signal is sensed during a sensing window defined relative to a reliably detectable cardiac cycle event in order to capture the passive and active filling phase signals. For example, diastolic sensing window 212 may be initiated relative to a delivered atrial pacing pulse or a sensed P-wave 208, which can be sensed using an atrial EGM signal, or relative to a ventricular sense or pace event. The event used for initiating sensing window 212 may be a right or left heart chamber event. Sensing window 212 may extend until a delivered LV pacing pulse or a sensed R-wave (intrinsic or evoked), which may be sensed using a ventricular EGM signal. The diastolic LV acceleration signal, sensed during diastolic sensing window 212, may be used to derive an optimization metric value representing diastolic function for use in determining an optimal pacing timing control parameter.

An LV pacing pulse can be delivered at a 140 ms AV delay following the sensed P-wave 208. In this case, the 140 ms AV delay results in separation of the passive and active filling phases as indicated by a distinguishable active filling phase signal peak 204 following the passive filling phase signal 202. The LV acceleration signal 200 sensed during diastolic sensing window 212 shown in FIG. 3 illustrates a number of diastolic metrics that may be used for determining an AV delay or other pacing timing control parameter. For example, separation of diastolic filling phases, as indicated by the greatest separation of the two left ventricular filling phases due to passive left ventricular relaxation and left atrial contraction, and a maximized atrial peak acceleration during sensing window 212.

At operation 304, the signal is compared to a baseline signal and/or baseline data stored in memory (e.g. RAM). Exemplary baseline data can be customized to a particular patient and/or determined through averaging data over a relevant population of patients. Detection of dysfunctional diastropy is accomplished by comparing data, obtained through one or more sensors on the IMD or lead, to baseline data stored in the memory of the IMD. Typically, a two standard deviation difference (i.e., that exists between the sensed signal and the baseline data is sufficient to establish diastolic dysfunction. Standard deviation is a widely used measurement of variability or diversity used in statistics and probability theory. Standard deviation shows how much variation or dispersion that exists from the average (e.g. mean or expected value).

Diastolic parameters that can be monitored or determined from monitored data includes E/A ratio, E/E', and E, and/or deceleration time can be used. Baseline data can be obtained from a population of persons that do not exhibit dysfunctional diastropy. Other parameters that may be relevant with respect to determination of diastolic dysfunction can include gender, age, blood pressure, cardiac condition or other suitable characteristic can be taken into consideration for determining a population. Averaging data associated with a relevant parameter(s) over a selected population can be used to determine baseline data. Alternatively, baseline data can be customized to a particular patient. To illustrate, baseline data can be obtained when the patient undergoes monitoring while determined to be free of dysfunctional diastropy. The baseline data from a patient may be equivalent to that of a healthy patient. Alternatively, the baseline data from patient may have a status that is less than healthy since HF patients may receive the IMD 14 after their health has deteriorated, which may not be the same or similar to the baseline data for a healthy patient. In the latter case, the baseline data may not be at an optimal value level; however, diastolic dysfunction can nevertheless be detected with less than healthy baseline data. After the baseline data is saved in memory such as RAM, the IMD 14 can then continuously sense data through the mechanical sensor disposed near tissue.

At operation 306, the compared data from operation 304 is then checked against diastolic dysfunction ranges, which are stored in memory (i.e. RAM). If the compared data falls outside the limitations of diastolic dysfunction for a particular parameter, then IMD 14 returns to monitoring signals at block 302. If the compared data falls within a range for diastolic dysfunction for a particular parameter, then, at operation 308, diastolic dysfunction data is determined to exist in the sensed signal. In one embodiment, diastolic dysfunction is determined to exist when two or more standard deviations exist between the baseline data and the sensed data related to a particular diastolic parameter. The determination of the presence of diastolic dysfunction through the method and IMD 14 described herein is performed without a sonographer. Additionally, computer instructions for IMD 14 can be configured to make determinations when a patient is considered to exhibit borderline diastolic dysfunction, which may be helpful for the patient and healthcare provider to develop a therapy or regime that helps the patient to avoid or forestall diastolic dysfunction. For example, the computer instructions can include ranges that are within 5% numerical range of exhibiting diastolic dysfunction. In another embodiment, the computer instructions can include ranges that are within 10% numerical range of exhibiting diastolic dysfunction.

Once diastolic dysfunction has been determined, a notification signal can be automatically generated and wirelessly sent through an antenna on IMD 14 to a receiver or computer of a healthcare provider and/or patient.

In one or more embodiments, IMD 14 delivers therapy to the patient in response to detecting diastolic dysfunction. Therapy can include delivery of electrical stimulation delivered through a medical electrical tissue to targeted tissue. In another embodiment, an agent (e.g. drug etc.) can be delivered to tissue.

IMD 14 continues to monitor signals from the patient to determine whether the therapy is reducing or eliminating diastolic dysfunction. In one or more embodiments, IMD 14 may automatically determine that the therapy should be adjusted (i.e. increased or decreased) with respect to electrical stimuli and/or drug delivery. Additionally, the therapy delivered to tissue can be automatically iteratively adjusted in response to monitored signals indicating that the therapy needs to be increased or decreased. Moreover, IMD 14 can also terminate therapy delivery if it has been determined that diastolic function is within a predetermined healthy or improved level of health.

Figure 5:
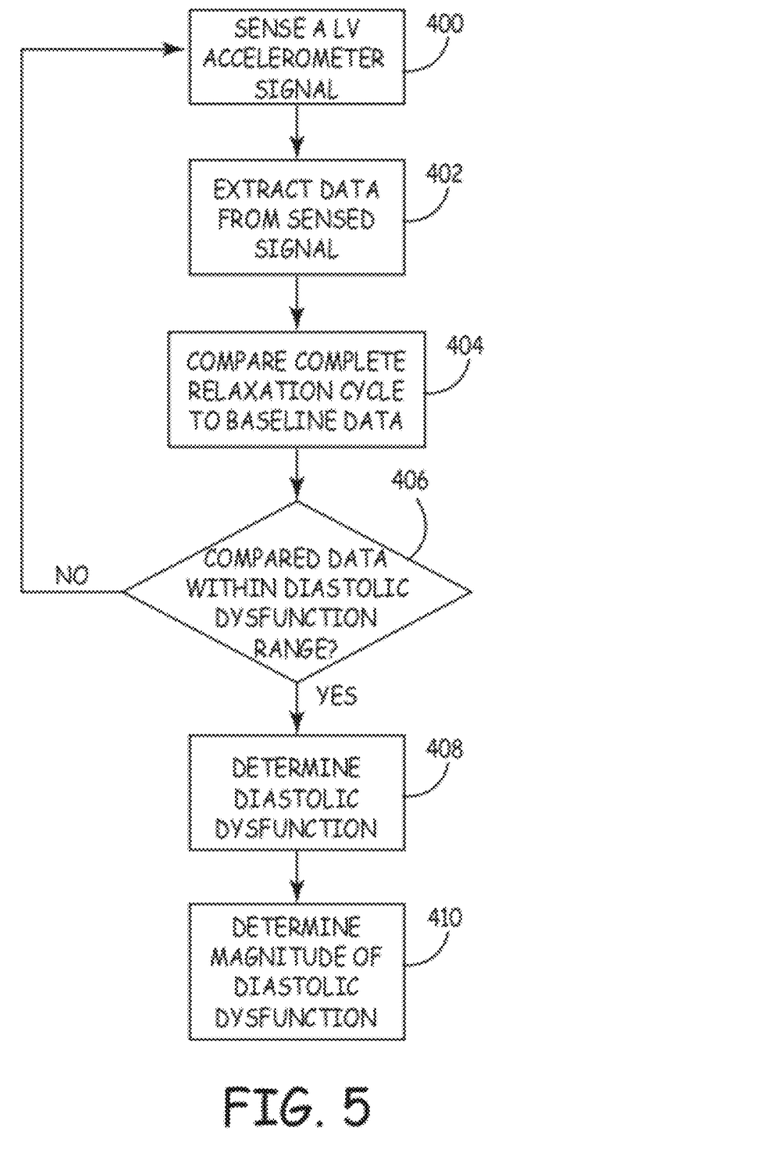
FIG. 5 is a flow diagram summarizing steps performed in a method for determining whether a patient exhibits diastolic dysfunction.

FIG. 5 is a flow diagram of an automated method to detect left ventricular lusitropy through a chronically implanted medical device connected to a medical electrical lead. The medical electrical lead includes a sensor at the distal end of the lead. The mechanical sensor is placed at or near a RV or a LV of a patient. At operation 400, the method comprises sensing a LV accelerometer signal through an implantable mechanical sensor affixed to the medical electrical lead. At operation 402, data is extracted of a complete relaxation cycle or period from the sensed LV accelerometer signal. At operation 404, the extracted complete relaxation cycle data is compared to baseline data. Template matching can be used to perform the comparison on the operation. In one or more other embodiments, waveform comparison can be performed. At operation 404, a determination is made as to whether diastolic dysfunction exists based upon comparing the extracted complete relaxation cycle data to the baseline data. At operation 406, a magnitude of the diastolic dysfunction is determined. Based upon the amount of deviation that exists between the data (e.g. complete relaxation period etc.) extracted from the LV accelerometer signal and the baseline data, the diastolic dysfunction can be quantified. Quantification of diastolic dysfunction in a patient can generally range from severe diastolic dysfunction, moderate diastolic dysfunction, to mild diastolic dysfunction. Thereafter, a notification signal can be automatically transmitted from the IMD to a healthcare provider and/or the patient.

Thus, a method and apparatus for determining and/or delivering therapy for left ventricular lusitropy have been presented in the foregoing description with reference to specific embodiments. It is appreciated that various modifications to the referenced embodiments may be made without departing from the scope of the present disclosure as set forth in the following claims.

The invention claimed is:

1. An automated method to detect relaxation abnormality in heart tissue through a chronically implanted medical device connected to a medical electrical lead, the method comprising:
    sensing a LV accelerometer signal through an implantable mechanical sensor affixed to the medical electrical lead, the mechanical sensor disposed at or near a right ventricle (RV) or a left ventricle (LV) of a patient;
    extracting complete relaxation period data from the LV accelerometer signal;
    comparing the extracted complete relaxation period data to baseline data; and
    determining whether relaxation abnormality in the heart tissue exists based upon comparing the extracted complete relaxation cycle data to the baseline data.

2. The method of claim 1, wherein the comparing step involves template matching.

3. The method of claim 1, wherein the comparing step involves waveform comparison.

4. The method of claim 1, wherein comparing step involves using a feature from the extracted complete relaxation cycle data.

5. The method of claim 1, further comprising quantifying a magnitude of the relaxation abnormality.

6. The method of claim 1, wherein the lead is placed endocardially in one of the RV and the LV.

7. The method of claim 1, wherein the lead is placed epicardially to one of the RV and the LV.

8. The method of claim 1, wherein the lead is placed intravascularly to one of the RV and the LV.

9. An automated method to detect relaxation abnormality in heart tissue through a chronically implanted medical device connected to a medical electrical lead, the method comprising:
    sensing a LV accelerometer signal through an implantable mechanical sensor affixed to the medical electrical lead, the mechanical sensor disposed at or near a right ventricle (RV) or a left ventricle (LV) of a patient;
    extracting data of a complete relaxation cycle from the LV accelerometer signal;
    comparing the extracted complete relaxation cycle data to baseline data;
    determining whether relaxation abnormality exists in the heart tissue based upon comparing the extracted complete relaxation cycle data to the baseline data; and
    quantifying a magnitude of the relaxation abnormality.

10. The method of claim 9 wherein the relaxation abnormality consists of left ventricular lusitropy.

11. The method of claim 9 wherein quantifying the magnitude of the relaxation abnormality consists of classifying the relaxation abnormality as one of a severe case, a moderate case, and a mild case.

12. The method of claim 9, wherein the lead is placed endocardially in one of the RV and the LV.

13. The method of claim 9, wherein the lead is placed epicardially to one of the RV and the LV.

14. The method of claim 9, wherein the lead is placed intravascularly to one of the RV and the LV.

15. The method of claim 9, wherein the lead is disposed in the coronary sinus.

16. The method of claim 9, further comprising:
    generating a notification signal to a receiver that relaxation abnormality is detected.

17. The method of claim 16, wherein the notification signal is transmitted to one of a healthcare provider and a patient.

18. The method of claim 9, wherein comparing step involves template matching the extracted complete relaxation cycle data to the baseline data which consists of a baseline complete relaxation cycle.

19. The method of claim 9, wherein comparing step involves waveform comparison.

20. The method of claim 9, wherein comparing step involves using a feature from the extracted complete relaxation cycle data.

21. The method of claim 9 wherein the baseline data is obtained from a patient.

22. The method of claim 9 wherein the baseline data is based on a population of patients.

* * * * *